(12) United States Patent
Shalon et al.

(10) Patent No.: US 8,870,953 B2
(45) Date of Patent: *Oct. 28, 2014

(54) DEVICES AND METHODS FOR TREATING SLEEP DISORDERED BREATHING

(71) Applicant: SVIP 7 LLC, Palo Alto, CA (US)

(72) Inventors: Tidhar Shalon, Palo Alto, CA (US); Guy Kotlizky, Kfar-Shemaryahu (IL)

(73) Assignee: SVIP 7 LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,871

(22) Filed: May 27, 2013

(65) Prior Publication Data

US 2013/0261763 A1 Oct. 3, 2013

Related U.S. Application Data

(63) Continuation of application No. 12/745,896, filed as application No. PCT/IL2008/001566 on Dec. 2, 2008, now Pat. No. 8,657,879.

(60) Provisional application No. 60/996,790, filed on Dec. 5, 2007.

(51) Int. Cl.
*A61F 2/20* (2006.01)
*A61F 2/82* (2013.01)
*A61F 2/04* (2013.01)
*A61F 5/56* (2006.01)

(52) U.S. Cl.
CPC ... *A61F 2/82* (2013.01); *A61F 5/56* (2013.01); *A61F 2/04* (2013.01)
USPC ............................................. 623/9; 623/23.64

(58) Field of Classification Search
USPC ............................................... 623/9; 128/898
See application file for complete search history.

(56) References Cited

U.S. PATENT DOCUMENTS

| 7,322,993 | B2 | 1/2008 | Metzger et al. |
| 7,909,037 | B2 * | 3/2011 | Hegde et al. .................. 128/848 |
| 8,657,879 | B2 * | 2/2014 | Shalon et al. ..................... 623/9 |
| 8,663,192 | B2 * | 3/2014 | Hester et al. .................. 604/514 |
| 2006/0157055 | A1 | 7/2006 | Pflueger et al. |
| 2007/0005024 | A1 | 1/2007 | Weber et al. |
| 2007/0246052 | A1 | 10/2007 | Hedge et al. |
| 2008/0035158 | A1 * | 2/2008 | Pflueger et al. ............... 128/848 |

(Continued)

FOREIGN PATENT DOCUMENTS

| DE | 10240725 A1 | 3/2004 |
| GB | WO 2007113586 A1 | 10/2007 |
| IL | WO 98/23233 A1 | 6/1998 |
| WO | WO 2009/072115 | 6/2009 |

OTHER PUBLICATIONS

Amended Claims Dated Aug. 22, 2010 to Communication Pursuant to Rules 161(2) and 162 EPC of Jul. 21, 2010 From the European Patent Office Re. Application No. 08857660.8.

(Continued)

*Primary Examiner* — Suzette J Gherbi
(74) *Attorney, Agent, or Firm* — Ash Tankha; Lipton, Weinberger & Husick

(57) ABSTRACT

Devices and methods of treating sleep disordered breathing are provided herein. The devices are designed capable of preventing collapse of an oral airway tissue during sleep while maintaining normal velopharyngeal functions.

11 Claims, 7 Drawing Sheets

(56) References Cited

U.S. PATENT DOCUMENTS

| | | | |
|---|---|---|---|
| 2008/0066769 A1 | 3/2008 | Dineen et al. | |
| 2008/0188947 A1 | 8/2008 | Sanders | |
| 2009/0078274 A1 | 3/2009 | Bhat et al. | |
| 2011/0144558 A1 | 6/2011 | Rousseau | |
| 2011/0265801 A1 | 11/2011 | Cullen | |
| 2012/0031412 A1 | 2/2012 | Metzger et al. | |
| 2013/0118505 A1* | 5/2013 | Rousseau et al. | 128/848 |
| 2013/0312767 A1* | 11/2013 | Gillis | 128/848 |
| 2013/0312768 A1* | 11/2013 | Flaherty et al. | 128/848 |
| 2013/0338700 A1* | 12/2013 | Matheny | 606/199 |

OTHER PUBLICATIONS

Communication Pursuant to Rules 161(2) and 162 EPC Dated Jul. 21, 2010 From the European Patent Office Re. Application No. 08857660.8.

International Preliminary Report on Patentability Dated Jun. 17, 2010 From the International Bureau of WIPO Re. Application No. PCT/IL2008/001566.

International Search Report Dated Apr. 20, 2009 From the International Searching Authority Re.: Application No. PCT/IL08/01566.

Notice of Allowance Dated Mar. 13, 2013 From the US Patent and Trademark Office Re. U.S. Appl. No. 12/745,896.

Official Action Dated Sep. 5, 2012 From the US Patent and Trademark Office Re. U.S. Appl. No. 12/745,896.

Official Action Dated Jan. 8, 2013 From the US Patent and Trademark Office Re. U.S. Appl. No. 12/745,896.

Official Action Dated Mar. 2012 From the US Patent and Trademark Office Re. U.S. Appl. No. 12/745,896.

Written Opinion Dated Apr. 20, 2009 From the International Searching Authority Re.: Application No. PCT/IL08/01566.

\* cited by examiner

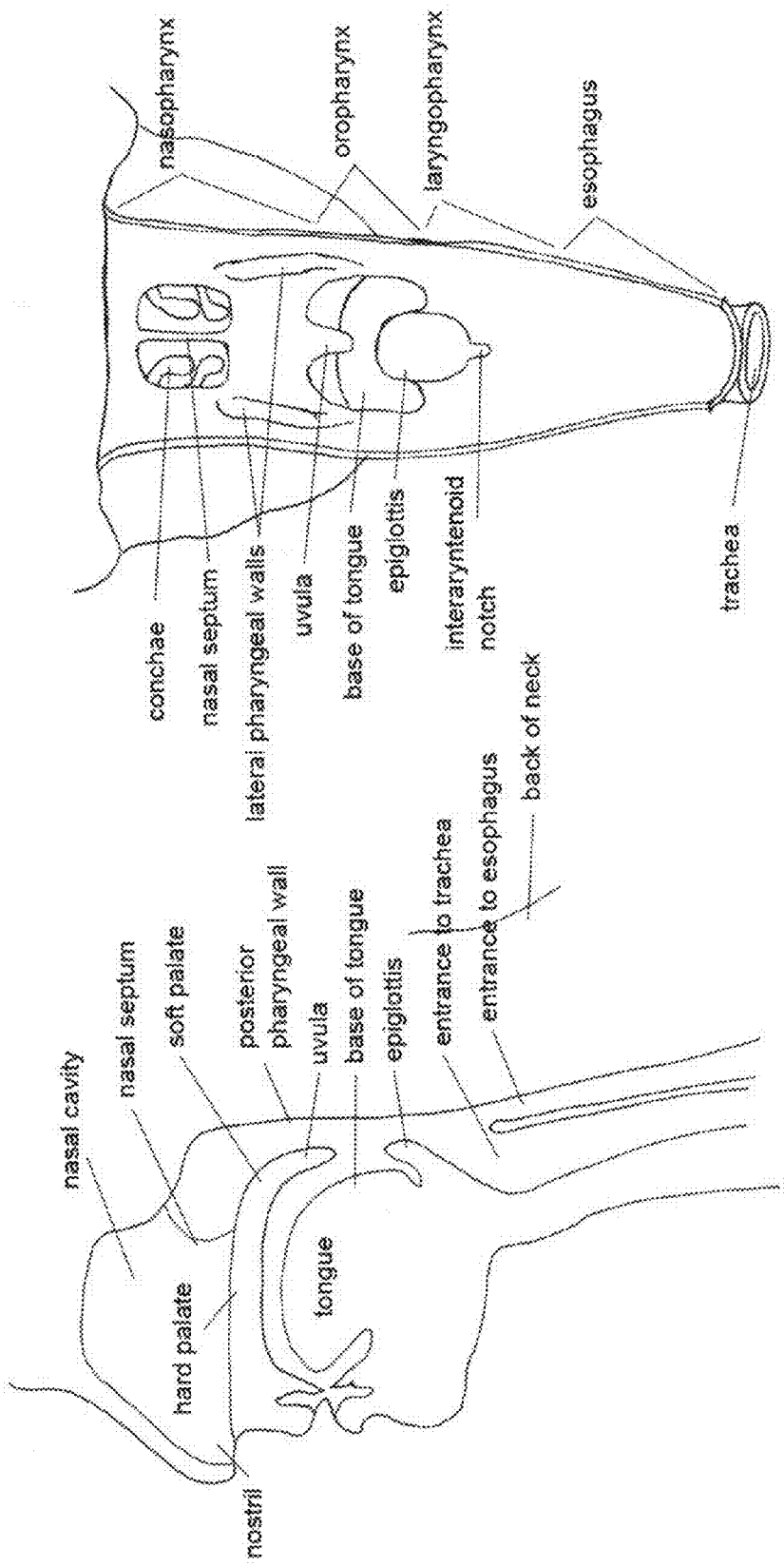

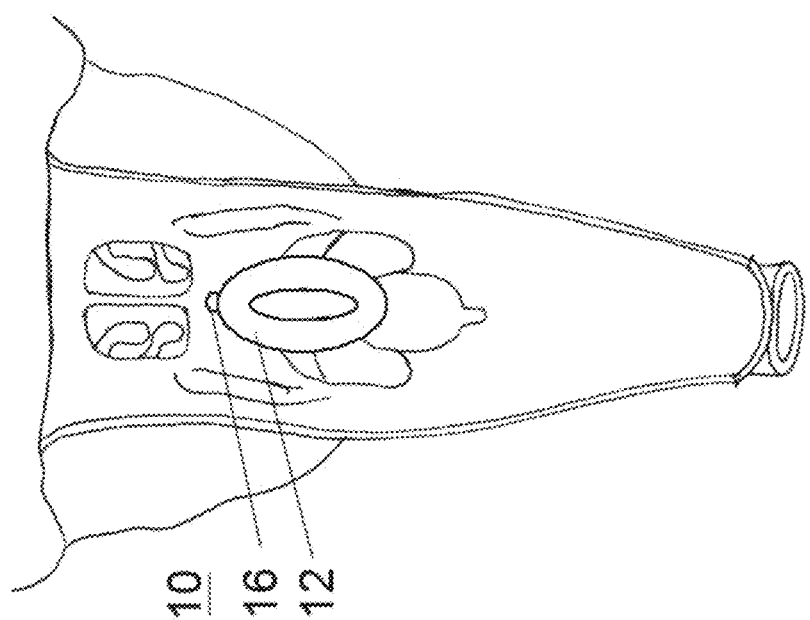
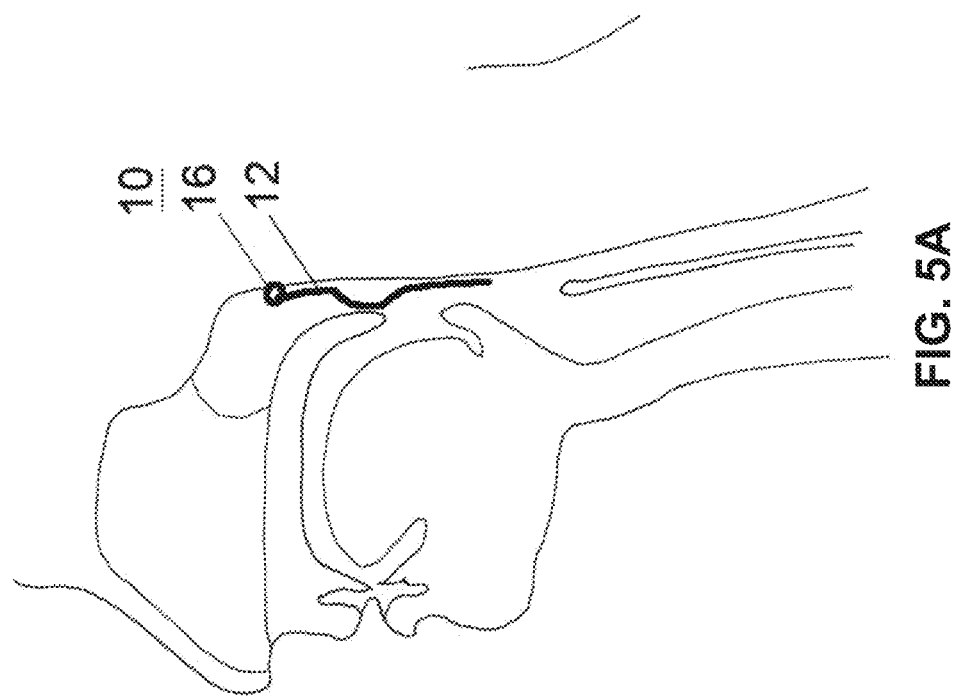

DEVICES AND METHODS FOR TREATING SLEEP DISORDERED BREATHING

RELATED APPLICATIONS

This application is a continuation of U.S. patent application Ser. No. 12/745,896 filed on Jun. 3, 2010, which is a National Phase of PCT Patent Application No. PCT/IL2008/001566 filed on Dec. 2, 2008, which claims the benefit of priority from U.S. Provisional Patent Application No. 60/996,790 filed Dec. 5, 2007.

The contents of all of the above documents are incorporated by reference as if fully set forth herein.

FIELD AND BACKGROUND OF THE INVENTION

The present invention relates to devices and methods for treating sleep disordered breathing and, more particularly, to devices which are designed for preventing collapse of airway tissue.

Snoring, excessive daytime somnolence, restless sleep, and obstructive sleep apnea (OSA) are manifestations of sleep-disordered breathing (SDB) which is characterized by abnormalities in respiratory patterns or the quantity of ventilation during sleep.

Obstructive sleep apnea, which is the most common SDB is caused by sleep time collapse of airway tissue forming the pharyngeal wall, soft palate, epiglottis, and/or tongue.

Postural muscle tone is highest in wakefulness, decreased in non-REM sleep, and minimal or absent in REM sleep. Collapse of tissues experienced during REM sleep, leads to a cycle of air flow obstruction, disruption of sleep and arousal.

The recurrent sleep arousal and associated intermittent hypoxia and hypercapnia have been implicated in the occurrence of adverse cardiovascular outcomes. In addition, there is evolving evidence that SDB may contribute to insulin resistance and other components of the metabolic syndrome.

Numerous efforts have been made to treat sleep disordered breathing. These include uvulectomy, nasal reconstruction, adenotonsillectomy, uvulopalatopharyngoplasty (UPPP), genioglossal advancement as well as more complex surgical approaches such as maxillary-mandibular advancement, bimaxillary advancement, and tongue-base surgery.

The type of intervention selected for treatment is based largely on patient physiology and anatomy. A patient with a large uvula who snores and has few or no symptoms of apnea may benefit from uvulectomy or from the Pillar™ implant which is used to stiffen the soft palate.

Relief of nasal obstruction alone rarely cures OSA, however, patient tolerance and response to nasal CPAP are often improved, thus septoplasty, septorhinoplasty, and turbinate reduction may be indicated in patients who have predisposing anatomy.

Adenotonsillectomy is often performed in the pediatric population to correct loud snoring and restless sleep.

Uvulopalatopharyngoplasty (UPPP) is a procedure which is performed most often for treatment of OSA. This procedure includes of tonsillectomy, reorientation of the anterior and posterior tonsillar pillars, and excision of the uvula and posterior rim of the soft palate.

Genioglossal advancement involves performing a mandibular osteotomy with anterior repositioning of the genioglossus-attached segment of the mandible. This procedure results in anterior displacement of the tongue.

Lingual tonsillectomy, lingualplasty, and laser midline glossectomy are procedures designed to reduce the mass of the tongue base. Temperature-controlled radiofrequency tissue ablation (TCRFTA) is used to reduce tissue mass of the tongue base and in the soft palate.

Despite considerable progress in our understanding of these disorders and the development of numerous treatment options, the principal therapeutic approach, continuous positive airway pressure (CPAP) which has been readily available since 1981 and exhibits poor patient tolerability and compliance remains the mainstay SDB treatment to this day.

There is thus a widely recognized need for, and it would be highly advantageous to have, an approach which is effective in treating sleep disordered breathing and yet is safe, minimally or non-invasive, reversible, and tolerable by patients.

SUMMARY OF THE INVENTION

According to one aspect of the present invention there is provided a device for treating sleep disordered breathing comprising a device body designed for positioning within a pharyngeal lumen and being designed and configured for: (a) maintaining an open airway during involuntary closure of the pharyngeal lumen; and (b) enabling sealing of the airway during swallowing.

According to further features in preferred embodiments of the invention described below, the involuntary closure of the pharyngeal lumen is caused by collapse of airway tissue during sleep.

According to still further features in the described preferred embodiments the device body is configured as a tube.

According to still further features in the described preferred embodiments a lumen of the tube is maintained open during sleep.

According to still further features in the described preferred embodiments a lumen of the tube closes during swallowing.

According to still further features in the described preferred embodiments the device body is configured as a double wishbone.

According to still further features in the described preferred embodiments the tube is configured capable of being crushed by a force of about 30 grams or less.

According to still further features in the described preferred embodiments the tube is selected having a length of 10-40 mm and a diameter of 3-12 mm.

According to still further features in the described preferred embodiments a lumen of the tube is selected having a diameter of 5-10 mm.

According to still further features in the described preferred embodiments the device further comprises an anchoring element attached to the device body, the anchoring element being anchorable to or within a nostril, a nasal cavity or nasopharyngeal tissue.

According to still further features in the described preferred embodiments the anchoring element is attached to the device body via a tether.

According to still further features in the described preferred embodiments the tether is selected having a length of 0.5-10 cm.

According to still further features in the described preferred embodiments the tether is an elastic tether.

According to still further features in the described preferred embodiments the tube is made from a material with a coefficient of friction of 0.2 or less.

According to still further features in the described preferred embodiments a lumen of the tube is coated by or fabricated from a hydrophobic substance.

According to still further features in the described preferred embodiments the device body, anchoring element and tether are selected such that when the anchoring element is anchored to or within a nostril, nasal cavity or a nasopharyngeal tissue, the device body resides within a nasopharyngeal or oropharyngeal lumen.

According to still further features in the described preferred embodiments the device further comprises at least one sinker element attached to the device body, the at least one sinker element being capable of extending down below a base of a tongue when the device body is positioned within a nasopharyngeal or oropharyngeal lumen.

According to still further features in the described preferred embodiments a distal end of the at least one sinker element is capable of extending into the gastrointestinal tract.

According to another aspect of the present invention there is provided a device for treating sleep disordered breathing comprising a device body designed and configured for minimizing resistance to airflow through collapsed airway tissue while enabling sealing of the airway tissue during swallowing.

According to still further features in the described preferred embodiments the device body is configured as a sheet or thin tube coated with or fabricated from a hydrophobic material.

According to still further features in the described preferred embodiments the device further comprises an anchoring element attached to the device body, the anchoring element being anchorable to or within a nostril, nasal cavity, or nasopharyngeal tissue.

According to still further features in the described preferred embodiments the anchoring element is attached to the device body via a tether.

According to still further features in the described preferred embodiments the hydrophobic material is PTFE.

According to still further features in the described preferred embodiments the hydrophobic surface functions in minimizing resistance to air flow.

According to still further features in the described preferred embodiments the device body is coated by or made from a material with a coefficient of friction of 0.2 or less.

According to yet another aspect of the present invention there is provided method of treating sleep disordered breathing comprising (a) positioning a device within a pharyngeal lumen, the device being designed and configured for: (i) maintaining an airway or minimizing resistance to airflow during sleep; and (ii) enabling sealing of the airway during swallowing.

According to yet another aspect of the present invention there is provided system for treating sleep disordered breathing comprising the device of the present invention and an applicator designed and configured for delivering and positioning the device within a pharyngeal lumen through the nose or mouth.

The present invention successfully addresses the shortcomings of the presently known configurations by providing a device capable of maintaining an open airway in collapsed airway tissue or minimizing resistance to airflow therein, especially during sleep and periods of loss of muscle tone.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A-B illustrate the relevant anatomy labeled in sagittal and posterior cut-away views.

FIGS. 5A-B illustrate positioning of a sheet embodiment of the device of the present device.

DESCRIPTION OF THE PREFERRED EMBODIMENTS

The present invention relates to a novel approach for treating sleep disordered breathing. Specifically, the present invention relates to devices and methods for minimizing resistance to airflow, or maintaining an open airway, through collapsed airway tissue while maintaining normal pharyngeal functions and being safe, reversible and highly tolerable for the patient.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Example. The invention is capable of other embodiments or of being practiced or carried out in various ways. Also, it is to be understood that the phraseology and terminology employed herein is for the purpose of description and should not be regarded as limiting.

Although numerous approaches for treating sleep disordered breathing are presently available, none are as effective as the continuous positive airway pressure (CPAP) approach which remains the gold standard of treatment.

However, due to low patient acceptability and compliance, alternatives to CPAP are constantly sought after.

Effective treatment is hindered by several factors. Although the soft palate, tongue and pharyngeal walls have all been implicated as potential targets for treatment, the involvement of these tissues in the etiology of the disorder varies from one individual to the next. In addition, since these tissues are also involved in activities such as swallowing and talking, modification thereof can lead to discomfort or reduced function during waking hours. Furthermore, the airway tissues are extremely sensitive to touch and mechanical forces in general. As these tissues are quite dynamic, any object coming into contact with them can cause significant discomfort unless properly designed and configured.

While reducing the present invention to practice, the present inventors realized that successful treatment of sleep disordered breathing can be achieved by maintaining a minimal airway opening or by minimizing resistance to airflow at the region of airway closure without directly manipulating airway tissue.

During sleep disordered breathing, pharyngeal and palatal tissues collapse to substantially reduce the patency of the airway at the lower nasopharyngeal and oropharyngeal regions. In individuals suffering from sleep disordered breathing such collapse can lead to complete closure of the airway and cessation of breathing.

Figure 1A:
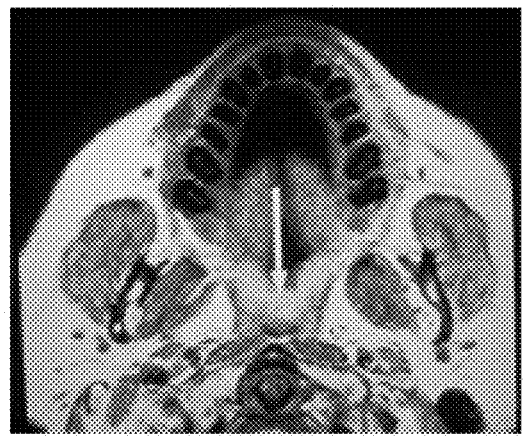
FIGS. 1A-B illustrate an MRI image of a transverse cross section at the level of the oropharynx showing an airway opening (black opening with arrow) in a collapsed state (FIG. 1A) and in an open state (FIG. 1B).
Figure 1B:

Studies have shown that airway muscle tissue loses tone intermittently when a person sleeps and that this loss of tone leads to collapse of this tissue and obstruction of the airway. As is illustrated in FIGS. 1a-b, collapse of pharyngeal tissues (including the lateral and posterior pharyngeal walls, the soft palate and the tongue) transforms the substantially round or oval airway opening into a narrow slit-like structure which is susceptible to further collapse and complete closure under the vacuum formed by a lung trying to expand. The narrow lumen forms a Bernoulli or venture tube, which further reduces the air pressure at the constriction and strengthens the seal. Furthermore, since airway tissue is covered with sticky mucus secretions, the seal between the hydrophilic tissues becomes airtight and is only relieved when the person awakens due to lack of oxygen, thereby restoring tone to airway tissues and as a result opening the airway.

FIG. 2a illustrates the relevant anatomy in a sagittal section while FIG. 2b illustrates the same anatomy in a posterior cut-away view where the posterior pharyngeal wall has been sliced open along its midline and the pharynx and esophagus opened to expose the relevant tissues looking from the back of the head towards the front (relevant tissues are labeled).

Experiments have shown that nasal airway tubes having an internal diameter as small as 3 mm (J S Nahmias et al., Chest 1988; 94; 1142-1147) can help bypass the blockage formed by airway tissue collapse during sleep and restore ordered breathing, however such tubes are meant to be rigid enough to self introduce every night, and therefore uncomfortable and not designed for long-term placement in the airway. From this experiment one learns that a device which can maintain an opening through the collapsed airway sufficient for supporting ordered breathing would be capable of treating sleep disordered breathing in a subject suffering from, for example, sleep apnea. However these experiments have also shown that traditional nasal airway tubes which are made rigid enough for direct intubation are highly intolerable and as such were not used long term by most of the patients in the study and are therefore not practical solutions to sleep disordered breathing.

As used herein, the phrase "airway tissue" refers to tissue which forms or surrounds the airway. Such tissue includes the tongue, the soft and hard palate, the uvula, the pharyngeal walls, pharyngeal mucosa, floor of the nasal cavity, nasal septum, nostrils, turbinates, tonsils, adenoids and related lymphoid tissues, epiglotis and any surrounding tissues including, the tonsillar pillars, the levator and tensor palatini muscles, and numerous other muscles (hyoglossus, styloglossus, stylohyoid, stylopharyngeus, palatoglossus, palatopharyngeus and pharyngeal constrictors) that have varying functions.

Thus, according to one aspect of the present invention there is provided a device for treating sleep disordered breathing in a subject, such as a human subject.

Figure 3B:
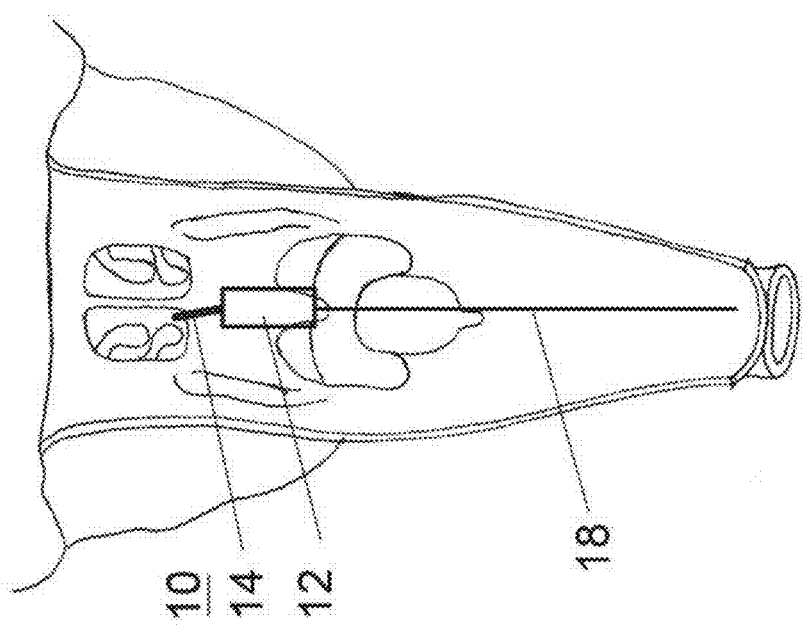
FIGS. 3A-B illustrate positioning of a tube embodiment of the present device.
Figure 3A:
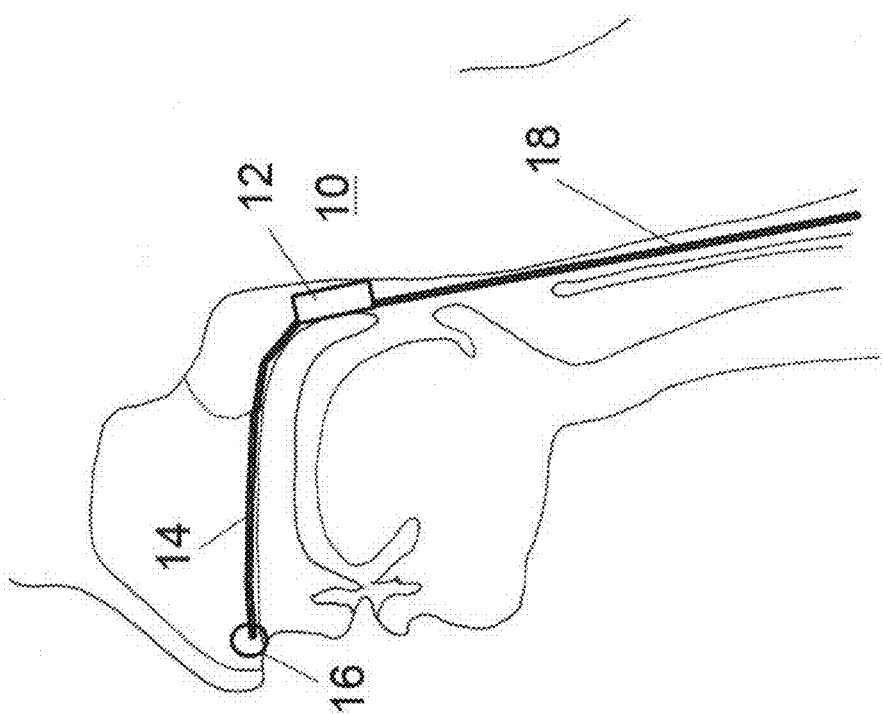

FIGS. 3a-b illustrate one preferred configuration of the present device which is referred to herein as device 10. Device 10 includes a device body 12 and tether 14 which is attached to device body 12 and anchoring element 16 (also referred to herein as anchor 16). Device body 12 and tether 14 are configured such that when anchor 16 is anchored to tissue, part of device body 12 remains in proximity to the uvula and as such provides an airway opening through the collapsed tissue.

Preferably, anchor 16 is anchored or attached to tissue in the nasopharynx, nasal cavity or nostril of the subject (specific anchoring schemes are described hereunder). In such cases, several approaches can be used to maintain device body 12 in the correct position. For example, a tether 14 constructed from a rigid (yet somewhat elastic) material can be configured to maintain device body in position and yet avoid contact with surrounding tissues. This can be achieved by curving a rigid portion of tether 14 (away from any tissue) and providing an elastic soft portion at the region of the soft palate; since the soft palate is dynamic, a rigid tether 14 impinging on a moving soft palate can result in discomfort to the subject.

Alternatively, tether 14 can be completely elastic and fabricated from, for example, a thin silicone tube. Due to the elasticity of tether 14, device body 12 of such a configuration can be displaced by forces such as the upward forces applied by the soft palate during a swallow as it seals the nasal cavity or the force of air upwards through the nasal cavity during a cough or sneeze. To ensure proper positioning under such forces, device 10 further includes one or more sinker elements 18 which act to maintain device body 14 in the desired position in the pharynx. Sinker elements 18 are attached to device body 12 opposite the point of attachment of tether 14 and act to counterbalance forces applied to device body 12 by upward movement of the soft palate for example. In an elastic tether configuration of device 10, movement of the soft palate during swallowing and talking would displace device body 12 up into the nasopharynx and therefore out of its functional position. Use of sinker elements 18 or another form of biasing element ensures that such forces are countered or dampened. Sinker elements 18 can extend down and hook around the forward edge of the arch of the soft palate or extend behind the base of the tongue (into the laryngopharynx), the epiglottis, the esophagus or into the stomach or even deeper into the GI tract. In the case of sinker elements 18 that extend into the GI tract, the distal ends (ends within the GI tract) of sinker elements 18 can be configured with an element for facilitating capture of sinker elements 18 by the peristaltic waves of the esophagus, stomach or duodenum in order to pull device body 12 into position. Such an element can be a ball or thickening in sinker elements 18 (for example a tassel-like distal end) which can be fabricated from a biodegradable/bioerodable material which disappears over time leaving only the lines themselves to provide a gentle traction force on device body 12.

Additionally, the resulting vector from the tension of tether 14, device body 12 and sinker element 18 creates a downward and forward force on the soft palate, also acting to open the airway and prevent the rearward collapse of the soft palate against the posterior pharyngeal walls.

Indeed, the entire device 10 or portions thereof can be biocompatible and dissolvable over time (for example made of a hydrogel) to degrade and disappear following their intended service time. Since the in vivo degradation time of such materials is well known in the art, design of device 10 or portions thereof capable of such timed degradation is well within the capabilities of the ordinary skilled artisan.

A device positioned between the soft palate and posterior pharyngeal wall provides several advantages when used in conjunction with sleep disordered breathing. Such a device is always positioned in the region of collapse thus ensuring that a patent airway is always maintained during sleep. In addition, the device is capable of maintaining an open airway under sleep-induced collapse (maintaining an outwards pressure on the tissue which is equivalent to approximately 10 cm of water) and yet collapses under greater tissue pressure (during swallowing and talking for example) thereby ensuring that velopharyngeal sealing functions are maintained. Finally, the device can have a non-stick or low coefficient of friction surface thereby ensuring that mucus secretions do not accumulate within the device and that peristaltic forces on device body 12 are minimized due to its low friction within the pharyngeal lumen. In addition, the fact that the tube shaped device collapses under swallowing pressures also ensures further cleaning by collapse-mediated purging of any material trapped within the tube. Device 10 can include a plurality of device bodies 12 working independently in parallel or in series or in combination to provide a patent airway during sleep.

According to one embodiment of the present invention, device body 12 is structured as a round or oval tube with an internal diameter of 2-10 mm, a wall thickness of 0.01-1.0 mm and a length of 1-4 cm. The device is positioned between the uvula and the posterior pharyngeal wall. Given that an open airway can be an oval with approximately 2-3 sq cm in cross sectional area during normal breathing, the device with a cross sectional area of 0.03-0.75 $cm^2$ is small enough to only tangentially touch an airway tissue and not interfere or apply forces on other parts of the airway during normal breathing. Such a device can be fabricated from silicone of various hardness (for example Shore A 0-100) or from another biologically compatible polymer such as for example polyurethane, latex or poly-tetrafluoroethylene (PTFE), metal such as titanium or alloys such as Nitinol (bare or covered with a polymer). In any case, the device is designed such that it resists a crush force of 5-50 grams, or preferably 10-25 grams per 2 cm length thereby being capable of supporting the pharyngeal walls against collapse during sleep and yet at least some portion of the tube flattens (crushes) and seals when greater pressure is applied thereto, by for example, pharyngeal wall pressure applied during swallowing, eating, speaking, coughing etc.

The numbers above are derived from the universal efficacy of 10 cm of $H_2O$ as delivered by modern CPAP machines which form an "air splint" that opens collapsed airways, mainly in the lateral direction, but also in the anterior posterior direction. Device body 12 is configured to provide similar uniform pressures on the collapsing airway tissues. For example, a 2 cm long by 6 mm diameter tube with a wall thickness of 0.35 mm made of silicone of shore A 60 can resist a crush force of approximately 30 grams. Another combination giving similar stiffness is a tube 2 cm long, 8 mm diameter with a wall thickness of 0.6 mm made out of shore A 5 as described later in Example 1. Such tubes are sufficiently stiff to provide a patent airway yet soft enough to not irritate sensitive airway tissue, and collapsible enough to form a seal that provides velopharyngeal sufficiency during swallowing, talking and coughing. Finding the right balance between proper stiffness and collapsibility is key to the functioning and tolerability of the present device.

Thus, any tube which can maintain such forces on the tissue at the region of collapse would be suitable for use with the present invention, provided such a tube would collapse under greater forces, such as those present during swallowing, eating or speech. As is further described hereinunder, the tube device utilized by the present device can be of universal fit, or custom fitted to each individual by measuring the tissue closure force at the region of interest using a manometer which can be temporarily introduced through the nostrils or oral cavity on a catheter or a handle. Device body 12 would then be constructed to be crushable/collapsible under such forces, but yet stiff enough to act as a "return spring" to outwardly displace airway tissues that have lost tone during certain stages of sleep.

In yet a further embodiment, device body 12 can include biasing elements that function to fix or bias its radial position in the lumen. For example, device body 12 can be centered using symmetrical elastic biasing elements extending radially from device body 12 or as a tube within a tube structure. Alternatively, device body 12 can be biased against one side of the lumen using an asymmetrical biasing element. An advantage of biasing device body 12 to the side is that it can be placed lower down the arch of the tonsillar pillar region without being grabbed and swallowed by the base of the tongue in the central higher portion of this "window" behind the uvula.

Device body 12 or portions thereof of this embodiment of the present invention can have a cross sectional shape of a circle, oval, D or eye-shaped and is positioned within an airway of the subject.

An additional configuration of device body 12 is substantially an open tube having a C-shaped cross section when uncompressed. Under the pressure exerted thereupon by pharyngeal and palatal tissues during sleep (induced by collapse of such tissues), the C-shaped device body 12 forms a closed tube which extends through the collapsed tissues thereby providing a path therethrough for air to flow from the nasal cavity into the trachea. Under greater forces, such as those present during swallowing and talking, the C-shaped tube flattens into a sheet (or the tissues fold in around the C shape) enabling sealing between the palate and posterior pharyngeal wall, thereby ensuring that normal velopharyngeal function is maintained. Alternative cross sectional area shapes of device body 12 are a tube-forming spiral, a sharp or wavy V, W, I-beam, star, or yin-yang shape. An additional configuration for device body 12 is a round or oval O-ring (or multiple O-rings arranged in a bird cage fashion) that is suspended in the pharynx behind the soft palate. The top portion of the O ring is used to tether or anchor it. The side portions apply sideways force to the lateral pharyngeal walls. The bottom portion of the O ring can serve as the sinker element behind the base of the tongue to keep the device positioned properly.

Device body 12 or portions thereof may be made of hydrophobic material and as such even a very thin flat or ridged sheet of hydrophobic material and/or material with a sufficiently low coefficient of friction may sufficiently reduce the sealing ability of the collapsed airway tissue, and therefore make it easier to restore airflow. In other words, it is easier to move air in between a hydrophobic surface and a tissue surface or between two hydrophobic surfaces than between two hydrophilic tissue surfaces of a moist airway that has collapsed. In essence, a hydrophobic device body 12 acts as a permanent "surfactant" or "non-stick surface" (non-wetting surface) in the pharynx and lowers the surface energy required to peel apart the collapsed portion of an airway and move air through it.

As used herein, "hydrophobicity" implies contact angle of water of >90 degrees, while superhydrophobicity implies contact angle of water of >150 degrees.

The surface energy property of the material used can be a function of the underlying material, its geometry or a combination of both. For example, polyester fibers coated with tiny silicone filaments form a superhydrophobic yet highly flexible surface (see Zimmermann et. al., Advanced Functional Materials V18, 22, 3662-3669, 2008). Various surface treatments, such as gas deposition or laser or plasma etching can be used to modify the free surface energy or contact angle of any particular material as is well known in the art.

Hydrophobic materials/coatings are advantageous in that they allow air to pass through the collapsed airway easily, do not allow water inside device body 12 to collapse the tube, do not clog with secretions since secretions will not adhere to inner walls and act to prevent device body 12 from being fouled with biofilms.

Suitable materials include PTFE (e.g. Teflon™) which has a contact angle of around 110 degrees and bare silicone which has a contact angle of ~90-110 degrees.

Device body 12 can be configured as a thin sheet rolled into a tight cylinder or "crumpled" by the collapsing airway. Such a configuration maintains enough of a passageway when collapsed or crumpled through small channels which enable air passage through the collapsing airway. Such small airways can "prime the flow" of larger volumes of air through a collapsed airway.

Alternatively, device body 12 can be one or more strips, sheets or a tube made of thin (0.5 to 50 mil thick) PTFE that is hydrophobic on both sides or made hydrophilic on the back surface (by etching or addition of a hydrogel for example). Such a device body 12 would adhere to the posterior and lateral pharyngeal walls. Preferably, the front surface of device body 12 is very hydrophobic (contact angle of water >90 degrees) and as such it provides a low friction surface for the uvula and tongue base thereby minimizing sensation and peristaltic forces trying to swallow device body 12. For example PTFE has a coefficient of friction of around 0.1, which minimizes the forces trying to swallow device body 12 in the oropharynx. Parts of device body 12 (or optionally sinker element 18) with higher coefficients of friction can extend down below the tongue base and be pulled down constantly against the tension of tether 14 and anchor 16 in the nasal cavity as per FIGS. 5a-b. During airway collapse, the hydrophobic surface of the PTFE sheet resting against the soft palate and tongue base would be easily peeled by air and allow the airway to open. Semi-rigid topographical features on this surface, such as little channels or ridges can also prevent a tight seal and help air pass through.

In yet another embodiment, the sheet has one or more central bumps, channels, gutters or parallel waves or ridges in the center or sides of otherwise flat device body 12. These bumps and protrusions can be a deformation of the same material from which device body 12 is made and can easily be formed by vacuum forming or molding technologies. These bumps, grooves ridges, channels, waves, and/or protrusions, collectively termed "topographical features" can protrude smoothly from the surrounding material and as a result would not cause any significant sensation when the pharyngeal walls, soft palate, uvula, tongue base or epiglottis rubs up against these structures. Optionally, these topographical features can be pressed flat during the forces present in the oropharynx during a swallow or while talking. Yet during loss of muscle tone, these topographical features allow for a minimal air channel (that can then expand into a full air channel) or gently force the soft palate and base of the tongue forward and/or lateral pharyngeal walls sideways, thereby allowing air to flow within or adjacent to these topographical features. In this configuration, device body 12 or a portion thereof can extend lower than the uvula so that a peristaltic force of the tongue and esophagus plays a role in keeping the sheet flat, taught and well positioned in the pharynx.

With respect to device 10 residing in the lumen of the airway, the minimal thickness of the sheet-shaped device body 12 enables it to be very tolerable. If device body 12 gets crumpled up during airway collapse, device body 12 folds on itself such that hydrophobic surfaces face other hydrophobic surfaces, thus minimizing resistance to air flow. Device body 12 in this embodiment can be made of any flexible hydrophobic or super-hydrophobic material, such as for example polyurethane, silicone and/or PTFE, or combinations of such polymers giving optimal softness, structural integrity and hydrophobicity. The sheet forming device body 12 can have very soft or rounded edges, such a silicone bumpers, to minimize discomfort of the edges as they contact sensitive airway tissue. The coefficient of friction of the materials or coatings used for device body 12 or portions thereof may be less than 0.5, preferably less than 0.25 and more preferably less than 0.15.

FIGS. 5a-b illustrate an embodiment of device body 12 which is constructed from an oval-shaped thin sheet of material with at least one hydrophobic surface and an oval-shaped central bump as the topographical feature that keeps gentle forward pressure on the uvula and soft palate. Device body 12 of this embodiment is depicted as being anchored to the posterior pharyngeal wall with anchor 16 that can take the form of any of the anchoring schemes described herein or known in the art. Device body 12 also is depicted as minimally extending into the oropharynx where the peristaltic forces of the tongue and other tissue helps keep it in position. It is also possible to combine device body 12 in this embodiment with the concepts of tether 14 and sinker elements 18.

In an alternative embodiment, device body 12 can be a thin (e.g. 0.001-0.5 mm wall thickness) polymeric tube with a cross sectional area of up to the open airway (e.g. ~1 to 4 sq cm) tethered via tether 14 to anchor 16 in the nasal cavity. Alternatively device body 12 can include a larger diameter semi-rigid ring along its top edge (proximal edge) that acts as anchor 16 to prevent downward migration of device body 12 in the pharynx, much like a contraceptive diaphragm or pessary is held in position in the vagina. In this embodiment, the structural stiffness of device body 12 is negligible in the fully open positions, but upon constriction of the pharyngeal opening the hydrophobic inner surfaces of device body 12 will not seal as tightly as collapsed airway tissue, and therefore air will pass through the airway through this "non-stick" lining. The outer layer of device body 12 in this configuration can be hydrophilic to attach itself to the airway tissues and act to keep the tube open. Alternatively, the tube can be made of a material (for example a thin PTFE extruded tube) that has sufficient rigidity to stay open while still being crushable elastically. Furthermore, the crumpling of device body 12 from its open diameter of around 5 to 25 mm to its fully constricted state during airway collapse will form wrinkles and ridges which will enable air to escape through the region of collapse. Mucous and other secretions will flow both around and within device body 12, whose opening is wide enough to not be clogged. Device body 12, if sized to take up most of the cross sectional area of an open airway (1-4 sq cm cross sectional area) will not move much within the airway and therefore not cause any major sensation. Furthermore, device body 12 can have a cutaway portion that does not extend behind the base of the tongue or the epiglottis to prevent the device from being swallowed. Alternatively, a region of device body 12 (for example the back surface) or sinker elements 18 can be exposed to the peristalsis of the tongue or esophagus to keep device body 12 properly positioned against the restraint of tether 14. The surface tension effect might be sufficient so that the mechanical stiffness of device body 12 can be negligible (e.g. as low as 1 mil or 0.02 mm thick silicone, polyurethane, polyetheretherketone (PEEK) and/or PTFE). In this fashion, device body 12 is not a stent in the traditional meaning of the word as device body 12 does not even need to touch the airway tissue under resting conditions, nor can device body 12 supply any significant radial forces on the tissue against which it is resting. Rather it acts as a collapsible "non-stick" surface or lining in the lumen of the airway.

Furthermore, the surface tension effects described above and mechanical effects of device body 12 that supply radial forces to prevent the total collapse of the airway can be utilized synergistically.

Device body 12 or portions thereof can be pleated, accordion-like, or have sections of varying cross sectional stiffness to accommodate changing axial and radial curvature of the anatomy or to provide preferential sites of elastic crushing (e.g. different shore hardness, different thickness walls, thin wall thicknesses stiffened with interspaced ribs or hoops, etc). Device body 12 or portions thereof can have flared ends (either in or out), slanted, flapped, thinned or rounded ends or ends of lower shore hardness to minimize any undesired mechanical stimulation of the airway tissue by the edges of device body 12. Device body 12 or portions thereof can have varying shore hardness layers to achieve the same effect (e.g. shore A 60 on the inside for mechanical stiffness and shore A 3 on the outside for a soft interface with the airway tissue).

Device body 12 can be collapsible to a flat profile during the day to minimize interference of the normal anatomy and assume a circular cross section during sleep based on a manually-activated mechanism or based on the automatic detection of apnea. For example, device body 12 can only open or inflate when a flow sensor inside it senses that no air is going through the device for a set period of time, at which point an actuator mechanically opens the tube or a mechanism inflates the device body into a shape that forms an airway or simply pushes away collapsed airway tissue to restore a patent airway. The device can contain on board electronics and actuators and be charged inductively through a conduction coil placed in the oral cavity for a few minutes a day, for example. Alternatively, the device can connect to a power or compressed gas source through a minimal connection at night. In an alternative embodiment, device body 12 can be inflated or stiffened through the transfer of gas or fluid though a manually or automatically activated pump mechanism (introduced into or present in the nasal cavity for example).

To prevent clogging, the device can be coated with a low coefficient of friction and hydrophobic material (e.g. Teflon™) or super-hydrophobic coatings (e.g. silicone fluorinated with fluoroalkylsilane), anti-fungal, anti-bacterial, anti-viral or other non-fouling coatings (such as Surfacine™), incorporate silver or other agents to keep the surfaces bacteriostatic or bacteriocidal, or be constructed so as to minimize clogging, fouling or the adherence of a biofilm by ensuring that the surface is extremely smooth (for example filler-free silicones cast in highly polished nickel-coated molds or extruded PTFE tubing). The occasional crushing of the tube closed against the airway tissue during routine swallowing and talking would force out any secretions in this short tube and therefore clean it. The device can also have openings in the tube along its length, ranging from 1% to 99% of the total open/closed surface area ratio. Such openings are designed for adding flexibility to the tube and minimizing clogging by enabling evacuation of any secretions, yet a device provided with such opening still maintains a general tube shape within collapsed tissues and thus maintains an open airway.

Furthermore, if device 10 inadvertently detaches from its anchor site or if device body 12 detaches from tether 14, there is the possibility of device 10 or portions thereof being aspirated or swallowed. To increase safety, all portions of detached device 10 can be made small enough not to fully obstruct an airway if aspirated, and can travel harmlessly through the GI tract and be removed from the body via defecation if swallowed. This feature is another advantage of utilizing the small and collapsible device body 12 of the present invention.

In a further embodiment, device body 12 or portions thereof can act as a reservoir of active agents (e.g. drugs), that can be eluted into the pharynx over time in a controlled manner. The active agent in device body 12 can be replenished from outside the body using a hollow tube forming tether 14. In this configuration, device 10 can function as a drug delivery system for indications such as sinusitis, sore throat, strep throat, tonsillectomy, throat surgery, viral and bacterial infections, and as a nasal drug delivery system in general. Examples agents that can be eluted, passively or actively released from device body 12 include antibiotics, antiviral drugs, local anesthetics, analgesics, peptides, hormones, small molecules and the like for either local or systemic delivery through the pharynx's mucosal surface. In one embodiment, device body 12 is an elastically inflatable reservoir present in the nasal cavity above the hard palate with tether 14 being a fill tube with a one-way check valve or septum interface and the active agent being dispensed through one or more orifices in device body 12. Control of the delivery of the active agent can be through active means (actuator) or passive means (pressurized flow through an orifice).

In one embodiment, device body 12 is connected to anchor 16 via tether 14. In an alternative embodiment, device body 12 can be connected directly to anchor 16 without tether device 14.

The present device can be anchored to any airway tissue using any of the following elements or combinations thereof: elastic or inelastic tethers, t-bar anchors, sutures, button-type anchors, hooks, magnetic clasps, cages, clips and the like. For example, anchoring elements can be delivered through the palatal tissue (at center by the uvula region or on the side by the tonsillar pillar) and anchored thereagainst using T-bar or button type stops preferably fabricated from a polymer such as silicone or a harder material coated with a polymer such as silicone. Such stops can be tethered to device body 12 using a polymer or they can be fabricated as an integral part of the device.

Anchor 16 can be attached to device body 12 directly or to an applicator (further described below), which can position anchor 16 in the appropriate place or be used to drive anchor 16 through the tissue.

The functionality of the present device can also be achieved by using different configurations of device body 12. For example, a device configured with stiffeners extending through the region of collapse can be used to maintain patency through collapsed tissue. Such a device can be configured as, for example, device body 12 which consists of a double wishbone which is fabricated, for example, from silicone coated Nitinol wire or a polymer such as polypropylene. Such a double wishbone configuration can be anchored to tissues above the soft palate, e.g. the nasal septum, via an anchoring ring or the like, and be sized and configured such that the wishbone arms extend through the region of collapse.

A straight piece of 0.01-0.02" diameter Nitinol wire (bent in a 4 cm long wishbone configuration) would supply enough force to maintain opening pressure on collapsed tissues (in the double wishbone configuration) and yet would bend under greater pressure (collapsing such that the distal ends of the wishbone touched or became very close to one another) thereby allowing closure of the palatal and pharyngeal tissues. Such a device can either be fully implanted as a stiffening arch or reside in the airway itself and apply pressure to the airway tissue.

Figure 4B:
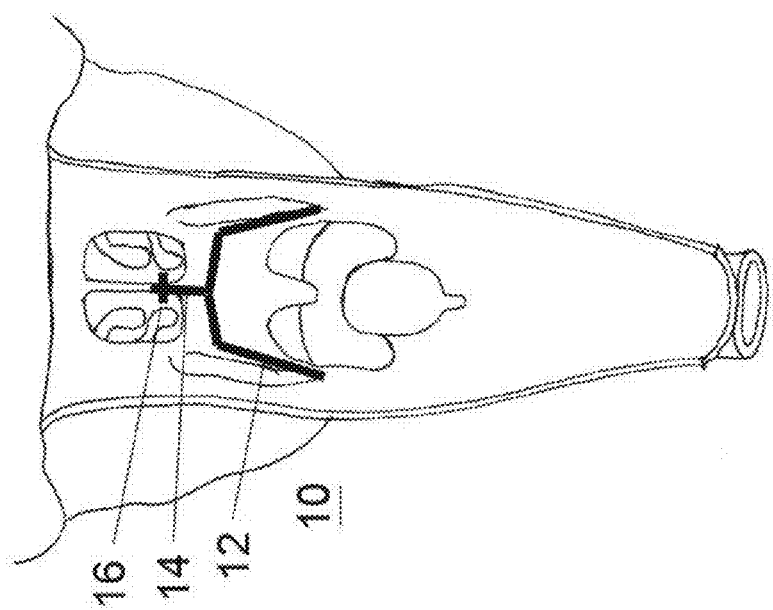
FIGS. 4A-B illustrate positioning of a wishbone embodiment of the device of the present device.
Figure 4A:
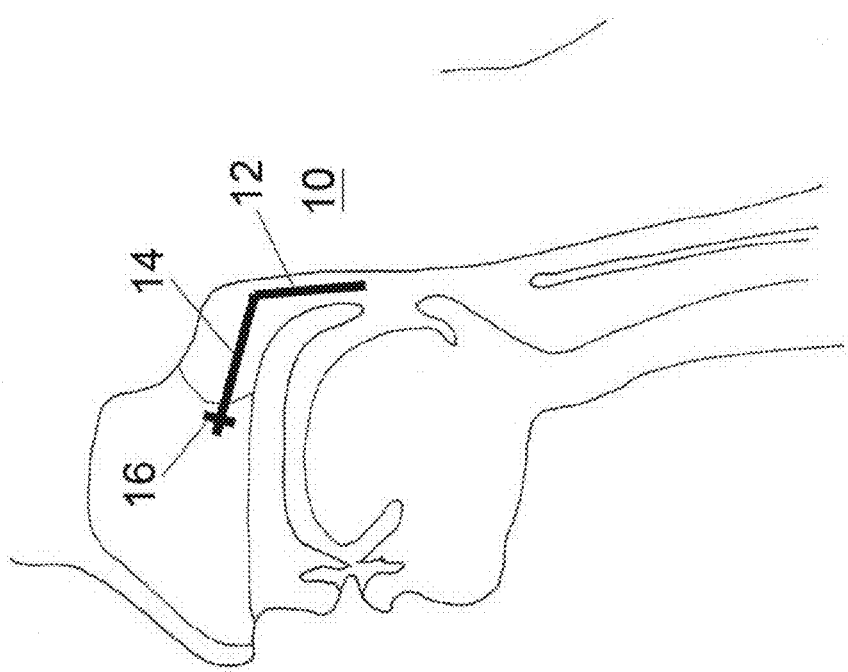

An example of a wishbone-like device which is referred to herein as device 10 is illustrated in FIG. 4a-b. In this embodiment device 10 has device body 12 consisting of wish-bone arms running from the septum down along the sides of the soft palate to a region close to the tonsillar pillars. Such a configuration applies gentle outward pressure on the lateral pharyngeal walls. The surface area of the distal arms of the wishbone device body 12 can be widened (e.g. form a loop or paddle) to maximize the surface area pressing against the airway tissues. The arms of the wishbone can go straight up the sides of the soft palate in the form of an inverted square U shape and not interfere with the raising and lowering of the center portion of the soft palate and uvula that occurs during swallowing and talking for example. Furthermore the arms of wishbone device body 12 can extend below the level of the uvula and still not be exposed to the back of the base of the tongue and the epiglottis since they are on the sides of the soft palate arch and not in the center of the "window" through which the base of the tongue contacts the posterior pharyngeal wall (best seen in FIG. 4b). Device body 12 can be attached via a short and semi-rigid tether 14 to the nasal septum with anchor 16 or use any other anchoring scheme described herein.

The applicator device used to introduce the wishbone device body 12 can keep the arms folded together using a retractable over-tube, or by keeping them bent together with a snare or water-dissolvable film until they are in position and ready to be deployed. This minimizes the size of device 10 as it is being introduced into the nasal cavity.

In the case where device body 12 is bulky, it is important to avoid having large areas of device body 12 contact the base of the tongue or the epiglottis, as that will inadvertently allow swallowing forces to pull device body 12 down and be uncomfortable for the user. If sinker elements 18 are used, they should be of minimal cross sectional area (e.g. thin strips or small diameter soft tubing) so as to not be felt by the user.

In an alternative configuration, there are more than two arms in the wishbone, thereby forming more of a bird cage or bent bow-tie shape. This configuration enables force in more than one radial direction (for example anterior-posterior in addition to lateral directions) and allows the distribution of forces on a great surface area.

Configurations anchored above the soft palate (e.g. to the nasal septum) can also utilize open or closed tube or tube-like configurations. Such configurations are preferably anchored such that they drop down along the lateral walls and thus provide an airway at the lateral sides of the natural airway opening. Alternative configurations of device body 12 providing such functionality can also be shaped as wedges rather than tubes. Such configurations can wedge apart collapsed tissues. For example, a V, L or I-beam-shaped device body which can be designed to wedge apart the corners of the collapsed airway (at the lateral pharyngeal walls) thereby providing an airway opening during tissue collapse.

It should be noted that device 10 of the present invention can also include a combination of the device body configurations described herein. For example, the upper portion of device body 12 can be a tube and the lower portion a wishbone so that the tube extends only as low as the uvula and the wishbones extend down the lateral pharyngeal walls into the oropharynx. The wishbone therefore also acts to center the tube of device body 12 in the airway. In another example, device body can be a thin sheet with a short tube section in the middle.

Effectively any structure that resides in the lumen formed in the lower portion of the nasopharynx behind the soft palate and optionally the oropharynx and prevents the collapse of airway tissue or reduces the surface energy required to move airway through the collapsed airway while not compromising the ability of the lumen to be sealed during swallowing is envisioned as a device body 12.

Any of the above described configurations can be delivered and positioned via the nose or the mouth. Such delivery can be effected using a dedicated applicator. For example, a 2 mm OD Tygon™ tube with an internal nylon line can be used to snare the distal end of device body 12 and/or sinker element 18. The delivery tube and loaded device 10 can be delivered together into the nasal cavity through a nostril. Device body 12 is small and collapsible so that it can deform to easily fit through the nostril and conchae. Once properly positioned in the back of the nasopharynx, oropharynx, laryngopharynx or esophagus, the internal nylon line forming the snare is pulled thereby releasing the distal end of device body 12 or sinker element 18. Swallowing will further pull on sinker element 18 and properly position device body 12 against the tension of anchor 16 and/or tether 14. The applicator tube is then removed from the nostril. Proper positioning of the device can be monitored through the nasal cavity with the use of a nasal endoscope or through the oral cavity using direct visualization or with the use of a mirror. Depth markings or mechanical stops on the applicator can help guide the user or physician to make the delivery at the appropriate position.

Alternatively, a soft, elastic and flexible tether 14 can be coated with a water-soluble material, such as a hydrogel like carboxymethyl cellulose (CMC) which is then dried to allow the physician or the user to push device 10 into the nostril without an applicator. The coating will dissolve in the moist environment of the nasal cavity and pharynx and tether 14 will return to being soft, elastic and flexible.

In a further embodiment, device 10 can be preassembled on an applicator and together they can lubricated with a lubricating gel such as KY™ and/or an anesthetic gel such as lidocaine and packaged.

Device 10 can also be designed to be introduced and removed by the user on a daily basis. The removed device is either discarded and a new one used or cleaned or disinfected for repeated use. Some portion of device 10 can dissolve or degrade after a set amount of time to encourage the replacement of the device. This approach helps to ensure that no bacteria or fungus colonize the device in the long term as it is frequently replaced.

The user can be tested using a manometer-equipped device which can be temporarily positioned at the region of interest and used to measure the forces needed to maintain patency during tissue collapse as well as the forces exerted during non-sleep functions such as eating, swallowing, coughing and talking. In addition, the test device can also be used to measure the length and diameter of the device body 12 needed, thereby enabling selection of an optimal device body 12 (from a kit which includes tethers of varying lengths, device bodies of varying sizes and crush strength).

The applicator can include an applicator head mounted on an operating handle. The applicator head can include a device engaging element(s) and one or more tissue penetrating elements for facilitating anchoring of the device into oral or nasal tissues. The applicator head can be introduced trans-nasally or trans-orally if mounted on a swivel joint which can assume a selected angle (0-180°) with respect to the operating handle of the applicator.

The anchor and the device can be separated into two components so that a low profile empty anchor can be installed, and then tethers or device bodies (e.g. tubes or wishbones) of varying lengths, size, geometry or stiffness can be positioned on the anchor. For example, device body 12 with sinker element 18 can be introduced through the nostril of a patient by a doctor and partially swallowed by the patient, intentionally placing device body 12 too deeply in the pharynx. Tether 14, whose proximal end remains outside the patient's nose, is pulled by the doctor until an alignment mark on device body 12 is visible through the open mouth of the patient. Cage anchor 16 (described below) is installed in the nostril of the patient by the doctor and tether 14 is clipped to cage anchor 16 and excess tether 14 is cut off to finish the procedure. The device and the anchor can be connected via a permanent or reversible element, such as a latch, suture or magnetic clasp. A conically-shaped, cylindrically-shaped, or two rings or C-shaped ribs connected by one or more short spines made of a biocompatible metal and/or polymer can also be constructed to fit elastically as a cage anchor 16 within a nostril while preventing migration further into the nasal cavity (see FIGS. 3a-b for an example cage anchor inside the nostril of a subject). Tether 14 can be attached to this cage anchor 16. The profile of this cage can be minimized so that it is not externally visible, does not obstruct airflow, can pass through a GI tract if inadvertently swallowed, and can be comfortable worn for many months. Grabbing the cage either directly or with a tab, pull string or dedicated removal tool allows complete removal of device 10 in a matter of seconds.

Alternatively, tissue penetrating elements can serve to penetrate the target tissue and deliver anchor 16 (which can be attached to device body 12 or tether 14) into the tissue thereby anchoring the device at the correct position. In one embodiment, anchoring is facilitated by a set of one or more needles which are pre-spaced and are introduced through the oral cavity from behind the soft palate or trans-nasally through the nostril. The needles are connected to the anchoring element, which can be a T-bar, barb, button, ball and the like.

Preferable locations to anchor include the fibrous cartilage at front of septum, the mucosal covered cartilage deeper in the septum, the vomer or perpendicular wall of the ethmoid bone in the back of the nasopharynx.

When anchored to soft tissue, device body 12 can be made out of a silicone tube out of which emerge two short silicone tethers with silicone buttons that are in turn overmolded onto a suture thread with is attached to a suture needle. The suture needle is pushed through the soft palate from behind. The suture pulls the buttons through the tissue to the anterior surface of the soft palate. The suture thread is cut and the device is then anchored to the back side of the soft palate with two silicone tethers that go through the tissue and terminate in two silicone buttons on the front side of the soft palate for a fully flexible and elastic tethering system that is capable of conforming to the dynamic anatomy of the soft palate. It is expected that the tunnel through the soft palate will re-epithelialize and therefore not be a tract for infection, much like a tract formed in the tongue when it is pierced by a tongue stud. Furthermore, the buttons can be cleaved for quick removal of the device for a fully reversible procedure.

The applicator can consist of a vacuum cup to suck in a known volume and depth of tissue and then penetrate this tissue with a needle, releasing an anchor 16 (such as a T bar) on the other side of the sucked-in tissue pocket or fold. The anchoring element running through the tissue pocket or fold can be traditional suture thread (such as polypropylene) or an elastic tether (such as silicone).

The tissue penetrating elements can include a needle, a slotted needle or a lancet. The tissue penetrating elements can move in and out of the applicator head and be actuated via a trigger release mechanism. Such a release mechanism can be triggered to forcibly push the tissue penetrating elements out of the applicator head and into the target tissue. The tissue penetrating element can also be configured to elute or deliver a local anesthetic such as lidocaine to provide for painless anchoring.

The applicator can further include a device release mechanism (e.g. plunger) for releasing the device once it is in the desired position within the tissue. Delivery and positing of the present device is preferably effected under local anesthesia, while airway tissue is under tone, and thus does not require the physician to manipulate tissue anatomy prior to administration of the device.

It may be advantageous to perform the procedure under local anesthesia and to temporarily reduce normal muscle tone on purpose, by inducing muscular paralysis by Vecuronium, or sedation using propafol for example, and thereby to allow the physician to determine the optimal device position based on the anatomy of the collapsed airway. Such temporary paralysis may also inhibit the gag reflex which will allow the physician better access to the airway tissues when performing the procedure without causing the patient to gag if done through the oral route. If delivery is done through the nostril in a trans-nasal route, there is usually no gag reflex. Collapsibility of the tissue can be determined in real time using the Mueller maneuver or by over or under pressurizing the airway in a controlled manner, and any such collapse-prone regions identified as a candidate implantation site.

Procedures performed under general anesthesia may require manipulation of tissue in order to mimic the anatomy present when the airway tissues have baseline muscle tone since general anesthesia relaxes muscle tissue and could lead to collapse of airway tissue.

Delivery of the present device can be monitored via direct visualization or via an endoscope positioned through the mouth or nose, this is particularly important in delivery through the oral cavity into the soft palate to avoid a situation where due to misalignment the implant protrudes into the nasal cavity instead of residing in the tissue of interest.

The present invention also envisages oral/nasal appliances for providing a patent airway and for modifying the position and stiffness of the soft palate.

Thus, according to another aspect of the present invention there is provided an airway appliance configured for modifying palatal tissue.

Three configurations of an airway appliance are envisaged herein. A first configuration includes a device body that resides behind the soft palate. In one embodiment, the device body is a short tube behind the soft palate similar to the configuration in FIGS. 3a-b. The device body is reversibly attached to the uvula or the arch of the soft palate on one end and a tether running up the nasopharynx on the other end. Tension on the tether keeps the tube snug on the back of the soft palate, even during its full range of motion. Tension can be applied to the tether prior to sleep and maintained throughout the sleep period via an automatic or manually effected shortening of the tether, through a clasp mounted on the septum near the nostril for example. Tension on the tether can be relieved during waking hours to enable natural speech and eating functions.

In an alternative embodiment, the top end of the tether can terminate in a ring or funnel or ribs that stays lodged in narrowing nasopharynx roughly at the height of the hard palate. In yet a further embodiment, the device body is anchored via a tether to external nostril using a nose-clip or internal nostril cage. The advantage of the above configurations is the totally non-invasive aspect of the anchoring that requires no tissue penetration.

In an alternative embodiment, the device body is free to slide along the tether via a manual or automatic mechanism. During waking hours, the device body resides above the soft palate in the nasal cavity where it does not interfere with soft palate and pharyngeal functions and at night or during an apnea event, it is lowered into position behind the soft palate to open the airway.

In a further embodiment, device 10 can take the form of a nasal-palatal appliance. The appliance includes tether 14 which runs from a nostril opening through the nasal airway, around the top of the soft palate and into the oral cavity where it is anchored. Tension on tether 14 pulls the soft palate forward and up and the lateral pharyngeal walls slightly sideways, thereby preventing collapse of this tissue during sleep. During waking hours the tension in tether 14 can be relieved to allow normal functionality of the soft palate. Tether 14 of the device can terminate in soft hooks that hook from behind around the front edge of the soft palate arch. Tether 14 or applicator can be rigid enough or biased in a forward arch to enable such hooks to be steered into position or elastically engage as soon as they emerge from behind the soft palate in a trans-nasal approach. Alternatively, tether 14 is anchored at an oral cavity anchor, such as a dental bridge or hard palate screw, for anchoring two elastic tethers 14 at each side of the top back side of the oral cavity. Tethers 14, which act as elastic slings, proceed around the tonsillar pillar area, back behind the soft palate and up through the pharynx and terminate in the nasal cavity at an anchoring point. The cross section of tether 14, or portions thereof, can be round, flat like a ribbon, or porous like a mesh to engage as much surface area as possible. The device, or portions thereof, can be made out of fully or partially elastic materials such as silicone or polyurethane. Tension on tether 14 is set to pull the soft palate up, forward and to the side, thereby restoring a patent airway. It is possible due to the elastic nature of the sling to find the minimum tension that allows for a patent airway at night while at the same time not interfering with the functioning of the airway anatomy during waking activities (coughing, swallowing, talking, etc). Alternatively, tether 14 can be tensioned differentially while awake or during sleep using a patient activated mechanism. Examples of such a mechanism include a finger-operated slider or length adjustment device mounted in the oral cavity, or a clasp anchored near the nostrils in the nasal septum that allows the user to grab the hidden end of tether 14 and pull it tight during sleep, leaving some portion of tether 14 exposed outside the nostrils. The latch is released upon awakening, thereby loosening the tether 14 and hiding the end of tether 14 in the nostril.

Another configuration of the device of the present invention utilizes a dental bridge for pushing up, pushing sideways or pulling forward any or all of the soft palate, uvula, tonsillar pillars and lateral pharyngeal wall. Such an appliance can include a pair of rearward projections, for example fabricated from Nitinol wire covered with silicone. These projections can be configured for projecting rearward and behind the airway tissue of interest. Optionally, this appliance can have two modes of operation, a day mode, in which the projections are sequestered within the appliance or otherwise disengaged from applying steady-state pressure on airway tissue, and a night mode in which the projections provide the desired support for the airway tissue of interest.

In this configuration, the device includes one or more elements for biasing the soft palate up and optionally forward. Such elements can be attached to a dental bridge which can be mounted on the molars of the user. The bridge and/or elements can be adjustable so to enable adjustment of force on the soft palate and toggling between day mode (no force on tissue) and night mode (biasing of tissue). Such toggling can be effected using a hinge or slider mechanism activated by the user manually or through a remote or by fabricating elements from bendable material (e.g. Nitinol). The device can also be fitted with an optional device body 12 such as a tube or wishbone (similar to that described in FIGS. 3a-b and 4a-b), thus also providing the functionality described in context with these embodiment of device 10. Device body 12 can be therefore supported behind the soft palate from below. In all the configurations above, the device can also be used on a temporary basis to measure forces, determine efficacy in reducing SDB, and assist in the proper selection of a more permanent implant, such as those described in FIGS. 3, 4 and 5.

It will be appreciated that although the present devices are described in context of treatment of breathing disorders such as apnea, such a device or a modification thereof can also be utilized to treat snoring since it can be used to modify the stiffness or dynamics of the relevant airway tissue and thus dampen the vibration or cushion the impact thereof during sleep related breathing. For example, in treating snoring, the tube embodiment of the present device can be modified into a sling or smaller profile bumper (solid or hollow) which reduces the vibration and hence the noise generated by the vibrating airway tissues. It is anticipated that any form of device 10 described herein is useful in reducing snoring as one aspect of sleep disordered breathing, in addition to its utility in treating obstructive sleep apnea.

As used herein the term "about" refers to ±10%.

It is expected that during the life of this patent many relevant biocompatible materials will be developed and the scope of the materials used in device 10 is intended to include all such new technologies a priori.

Example 1

Visualization of a Tethered Airway Device in a Subject

Figure 6:
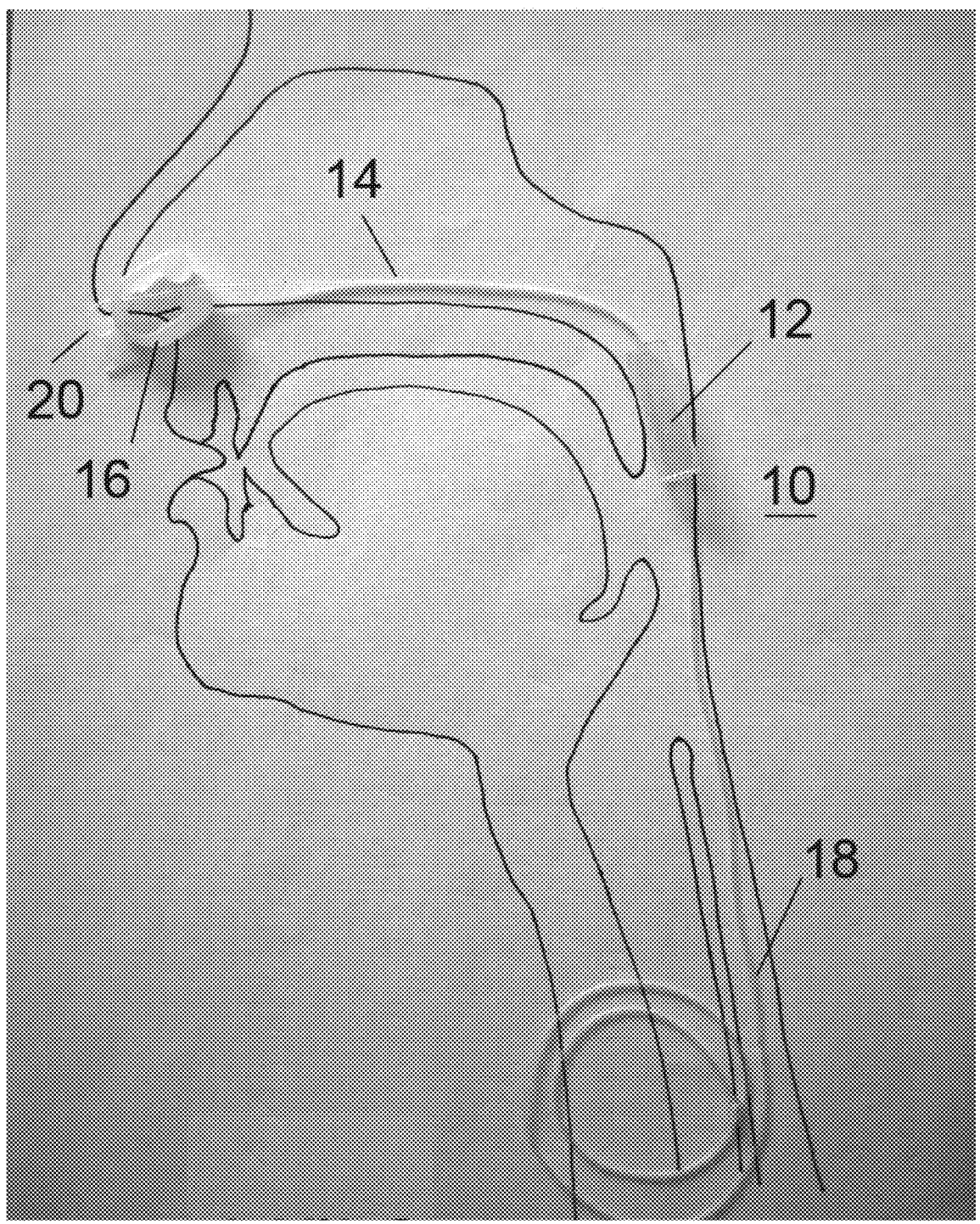
FIG. 6 illustrates the device described in Examples 1 and 2 overlaid on a sagittal view of the relevant anatomy and FIG. 7 is an endoscopic image showing a view down through the present device and into the airway of a subject.

The device illustrated in FIG. 6 (without sinker element 18) was constructed and delivered in accordance with the teachings of the present invention and positioned with a nasopharyngeal cavity of a male test subject. Device body 12 was made from a tube 2 cm long, 8 mm in diameter and 0.6 mm thick molded from silicone of shore A 5 and adhered to tether 14. Device body 12 was observed using in-vitro bench testing to crush closed when a 30 gram weight was placed on it with the weight uniformly distributed along the length of device body 12. 30 grams of crush force on the tube of device body 12 corresponds to a pressure of 20 cm of water, which is more than the universally effective CPAP pressure of 10 to 15 cm of water. Therefore device body 12 is stiff enough to prevent airway collapse.

Tether 14 was fabricated from a 1 mm OD silicone tube made from shore A 60 silicone. Attachment of tether 14 to device body 12 was via Wacker E41 silicone adhesive. Tether 14 was attached to anchor 16 (an external nose clip fabricated from silicone).

Device 10 was positioned using a 2 mm OD Tygon™ tube applicator (not shown) with a snare formed on its distal portion by an internally placed nylon line inside the Tygon tube. The snare attached both device body 12 to the applicator tube. The applicator and attached device 10 were introduced through a nostril of a male volunteer. Device body 12 was easily delivered though the nostril with no discomfort to the subject. Local anesthesia was not required. Anchor 16 (nose clip) was attached to the bridge between the nostrils of the subject and the length of tether 14 was adjusted using adjustment loop 20 so that device body 12 rested at the height of the uvula as verified using direct visualization of device body 12 through an open oral cavity. The subject reported no discomfort while device 10 was in the proper position.

Figure 7:
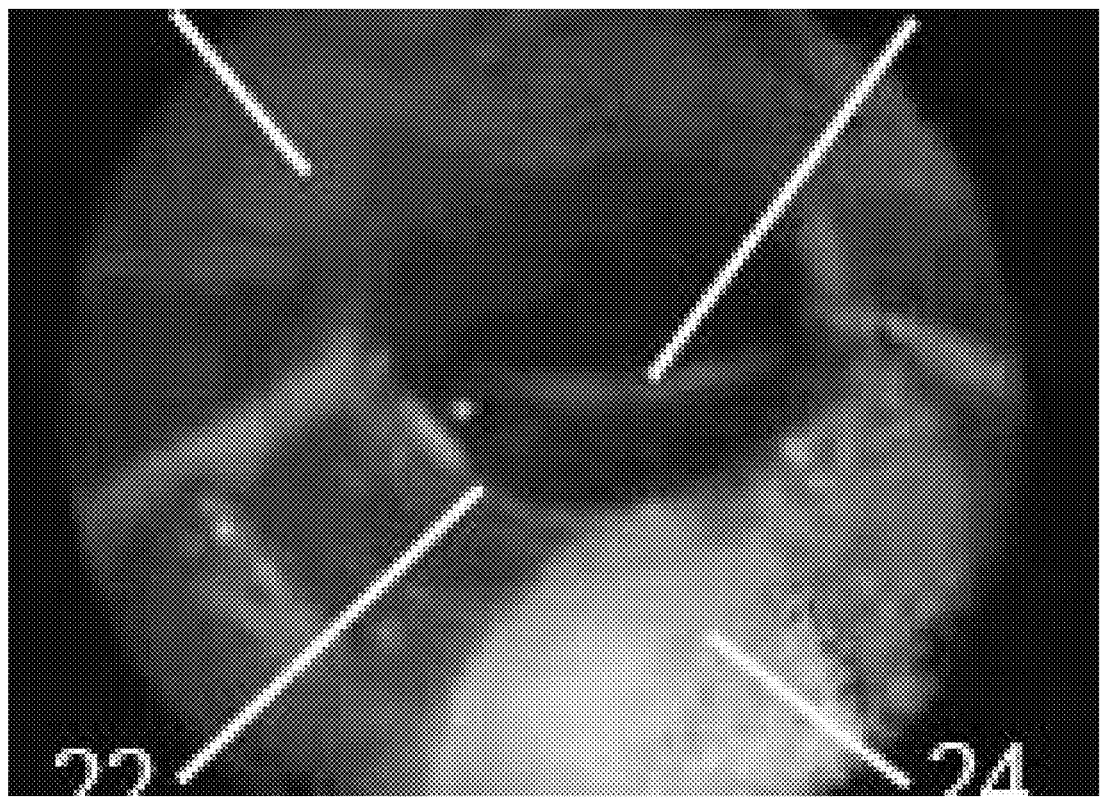

A pediatric nasal endoscope was introduced through the nostril and used to visualize device body 12 in the nasopharynx from above. The nasal endoscope was positioned just inside the top opening of device body 12 and the inner lumen of device body 12 was verified to be open as illustrated in FIG. 7. In FIG. 7, the inner lumen of device body 12, distal round bottom opening 22 of device body 12, uvula 24 viewed through transparent device body 12 and epiglottis 26 are all visible in the endoscopic picture. When the subject swallowed or talked, the inner lumen of device body 12 was observed to be crushed closed between the soft palate and the posterior pharyngeal wall, thereby confirming velopharyngeal sufficiency and crush force of great than 30 grams. The subject reported no discomfort during this procedure, even while swallowing or talking. Therefore it was demonstrated that the present device has sufficient force to maintain a patent airway during sleep and airway collapse yet still is crushable enough to maintain velopharyngeal sufficiency during swallowing with high patient tolerability. The nasal endoscope and device 10 were removed to conclude the experiment.

Example 2

Use of a Tethered Airway Device in a Patient

The device illustrated in FIG. 6 was constructed and delivered in accordance with the teachings of the present invention and positioned with a nasopharyngeal cavity of a male test subject suffering from snoring and sleep apnea. Device body 12 was made from a tube 2 cm long, 8 mm in diameter and 0.6 mm thick molded from silicone of shore A 5 and adhered to tether 14. Tether 14 was fabricated from a 1 mm OD silicone tube made from shore A 60 silicone. Attachment of tether 14 to device body 12 was via a Wacker E41 silicone adhesive. At the distal end of sinker element 18 which measured 50 cm in length, a 4 mm ball of silicone was formed using the silicone adhesive. The 4 mm ball provided an object against which peristaltic forces worked to cause sinker element 18 to be swallowed and present in the stomach of the subject, thereby aligning device body 12 in the pharynx. Tether 14 was attached to anchor 16 (an external nose clip fabricated from silicone).

Device 10 was positioned using a 2 mm OD Tygon™ tube applicator (not shown) with a snare formed on its distal portion by an internally placed nylon line inside the Tygon tube. The snare attached both device body 12 and the distal end of sinker element 18 to the applicator tube. The applicator and attached device 10 were introduced through a nostril of the male patient. Device body 12 was easily delivered though the nostril with no discomfort to the subject. Local anesthesia was not required. When sinker element 18 was in the upper esophagus, the snare was released and the applicator tube slowly removed. Sinker element 18 was then swallowed by the subject along with a few sips of water. Anchor 16 (nose clip) was attached to the bridge between the nostrils of the subject and the length of tether 14 was adjusted using adjustment loop 20 so that device body 12 rested at the height of the uvula as verified using direct visualization of device body 12 through an open oral cavity. The subject reported no discomfort while device 10 was in the proper position.

The subject spent the day with device 10 in position and indicated no problems in eating, drinking, swallowing, breathing or talking. The subject then slept with device 10 installed. A video and audio recording of the night's sleep indicated that the subject did not snore nor did he enter into any apnea events. The subject spent most of the night on his back, which is a challenging position as most snoring and apnea events are made worse in the supine position due to the weight of the tongue and other tissues pushing back on the airway. The subject awoke refreshed in the morning, reported no discomfort from the device and reported that he could have continued wearing the device indefinitely. At the conclusion of the experiment, the subject removed the device by pulling out device body 12 through the nostril using tether 14 in a matter of seconds. The example above shows that the present invention successfully addresses the shortcomings of the presently known art by providing an air pathway through collapsed airway tissue during sleep with a device that is safe, non-invasive, reversible, tolerable and effective during both waking and sleeping hours.

It is appreciated that certain features of the invention, which are, for clarity, described in the context of separate embodiments, may also be provided in combination in a single embodiment. For example, any device body, tethering, anchoring or delivery embodiment, configuration or scheme can be combined with each other to create a device that achieves all of the functions described herein. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for treating sleep disordered breathing comprising a tether having a first end attached to an anchor, and a second end attached to a device body configured as one of a sheet, an open tube and a closed tube, said tether being capable of suspending said device body within a pharyngeal airway, said device body being designed and configured for one of maintaining patency of said airway and minimizing resistance to airflow during involuntary closure of said airway tissue, wherein at least a portion of the device includes a hydrogel.

2. The device of claim 1, wherein said tube is configured capable of being elastically closed by a radial force of one of about 30 grams and less.

3. The device of claim 1, wherein said tube is selected having a diameter of 3-12 mm.

4. The device of claim 1, wherein said tube is selected having a length of 10-40 mm.

5. The device of claim 1, wherein at least some portion of said device body is comprised from a hydrophobic material.

6. A method of treating sleep disordered breathing comprising:
 (a) inserting a device including a tether having a first end attached to a device body through a nostril;
 (b) suspending said device body within a pharyngeal airway, said device being designed and configured for one of maintaining patency of said airway and minimizing resistance to airflow during sleep; and
 (c) anchoring said tether, thereby treating sleep disordered breathing.

7. The method of claim 6, wherein said device body is one of a sheet, an open tube and a closed tube.

8. The method of claim 6, wherein (a) is effected via an applicator attached to said device.

9. The method of claim 6, wherein said device body is suspended one of behind the soft palate ending at the level of uvula and above the level of the uvula.

10. The method of claim 7, wherein said tube is selected having a diameter of 3-12 mm.

11. The method of claim 7, wherein said tube is selected having a length of 10-40 mm.

* * * * *